United States Patent
Wang

(10) Patent No.: US 7,370,689 B2
(45) Date of Patent: May 13, 2008

(54) THERMO CHROMIC HEAT STORING/RELEASING DEVICE

(75) Inventor: Ching-Chuan Wang, Yungho (TW)

(73) Assignee: Wei-Hsun Wang, Taipei Hsien (TW)

( * ) Notice: Subject to any disclaimer, the term of this patent is extended or adjusted under 35 U.S.C. 154(b) by 471 days.

(21) Appl. No.: 10/871,059

(22) Filed: Jun. 21, 2004

(65) Prior Publication Data
US 2005/0230084 A1 Oct. 20, 2005

(30) Foreign Application Priority Data
Apr. 14, 2004 (TW) ................ 093110346

(51) Int. Cl.
*F28F 23/00* (2006.01)
*B65D 85/00* (2006.01)

(52) U.S. Cl. ........... 165/11.1; 165/10; 165/905; 206/459.1

(58) Field of Classification Search ........ 165/10, 165/11.1, 80.1, 905; 206/459.1; 426/88; 604/361
See application file for complete search history.

(56) References Cited

U.S. PATENT DOCUMENTS

| 5,389,093 | A | * | 2/1995 | Howell | 604/361 |
| 5,545,198 | A | * | 8/1996 | Owens | 607/108 |
| 2004/0142070 | A1 | * | 7/2004 | Haen | 426/87 |
| 2004/0154947 | A1 | * | 8/2004 | Duranton | 206/459.1 |

* cited by examiner

*Primary Examiner*—Ljiljana Ciric
(74) *Attorney, Agent, or Firm*—Troxell Law Office, PLLC

(57) ABSTRACT

A thermal chromic heat storing/releasing device includes a bag having an enclosed space for containing a heat storing/releasing material, and the heat storing/releasing material is a material that can store and release heat and the heat storing/releasing material is contained in the bag. A thermal chromic printed layer having at least a part disposed on the bag, and the printed material is mixed with a thermal chromic dye, such that the thermo chromic material will change the color of the printed layer for a visual indication as the temperature rises or drops.

7 Claims, 3 Drawing Sheets

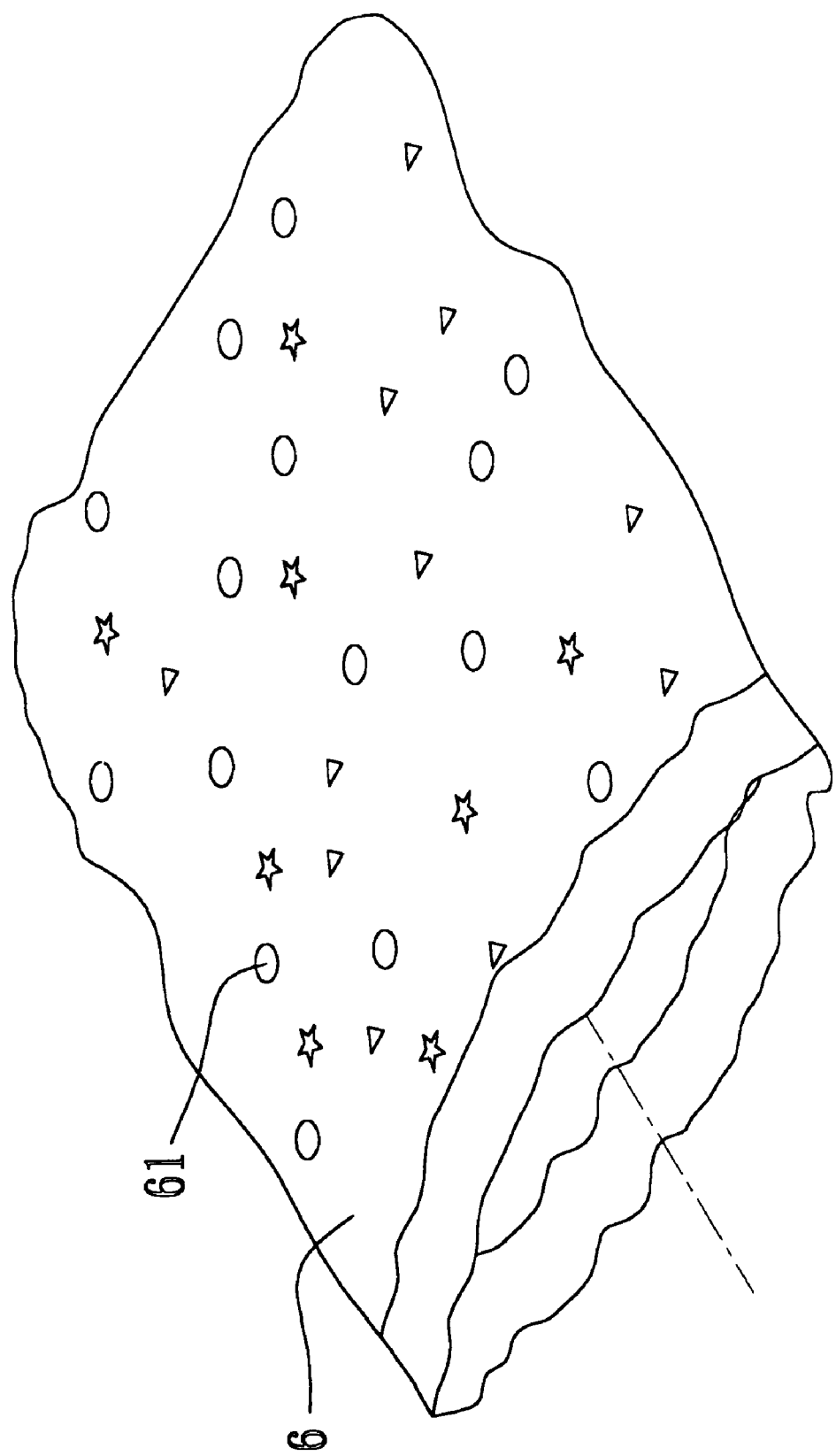

US 7,370,689 B2

THERMO CHROMIC HEAT STORING/RELEASING DEVICE

BACKGROUND OF THE INVENTION

1. Field of the Invention

The present invention relates to a thermal chromic heat storing/releasing device, more particularly to a heat storing/releasing device containing a thermal chromic material or its bag having a printed material with thermal chromic dye, such that the heat storing/releasing device changes its color as the temperature rises, and it resumes its original color as the temperature drops.

2. Description of the Related Art

As the heat storing/releasing device has been used for keeping us warm or for the health care purpose, there are various methods such as the traditional way of providing heat after water is heated and the heat is released successively during the temperature drop period. A metal starter is installed in a hot pack, such that the starter activates the solution in the hot pack to produce heat, and provides heat in the processes from heating to cooling.

The present inventor has disclosed a starter for the nebulising process to activate the rise or drop of the temperature of a saturated sodium acetate solution as described in the R.O.C. Utility Model Patent No. 146,156. Such patented technology has gained good reputations in the market after its being used for some time.

As mentioned, the basic objective of a heat storing/releasing device is to provide heat for warming us up or for the health care purpose. Therefore, the heat produced is a key issue, and the prior-art heat storing/releasing device does not come with a mechanism to indicate the quantity of heat produced except by the sensing of our skin. If a user is a patient or a person who falls sound asleep, then the user has no idea on the quantity of heat produced, and thus its application is not good enough.

SUMMARY OF THE INVENTION

In view of the foregoing shortcomings of the prior art, the inventor of the present invention based on years of experience on engaging in the business of the heat storing/releasing device conducted extensive researches and experiments, and finally invented the thermo chromic heat storing/releasing device in accordance with the present invention.

In order to achieve the objective set forth, a thermal chromic heat storing/releasing device in accordance with the present invention, comprises a bag having an enclosed space for containing a heat storing/releasing material, and the heat storing/releasing material is a material that can store and release heat and the heat storing/releasing material is contained in the bag; a thermal chromic printed layer having at least a part disposed on the bag, and the printed material is mixed with a thermal chromic dye, such that the thermo chromic material will change the color of the printed layer for a visual indication as the temperature rises or drops.

BRIEF DESCRIPTION OF THE DRAWINGS

FIG. 3 is a perspective view of the thermo chromic heat storing/releasing device being according to a preferred embodiment of the present invention.

DETAILED DESCRIPTION OF THE PREFERRED EMBODIMENTS

Figure 1:
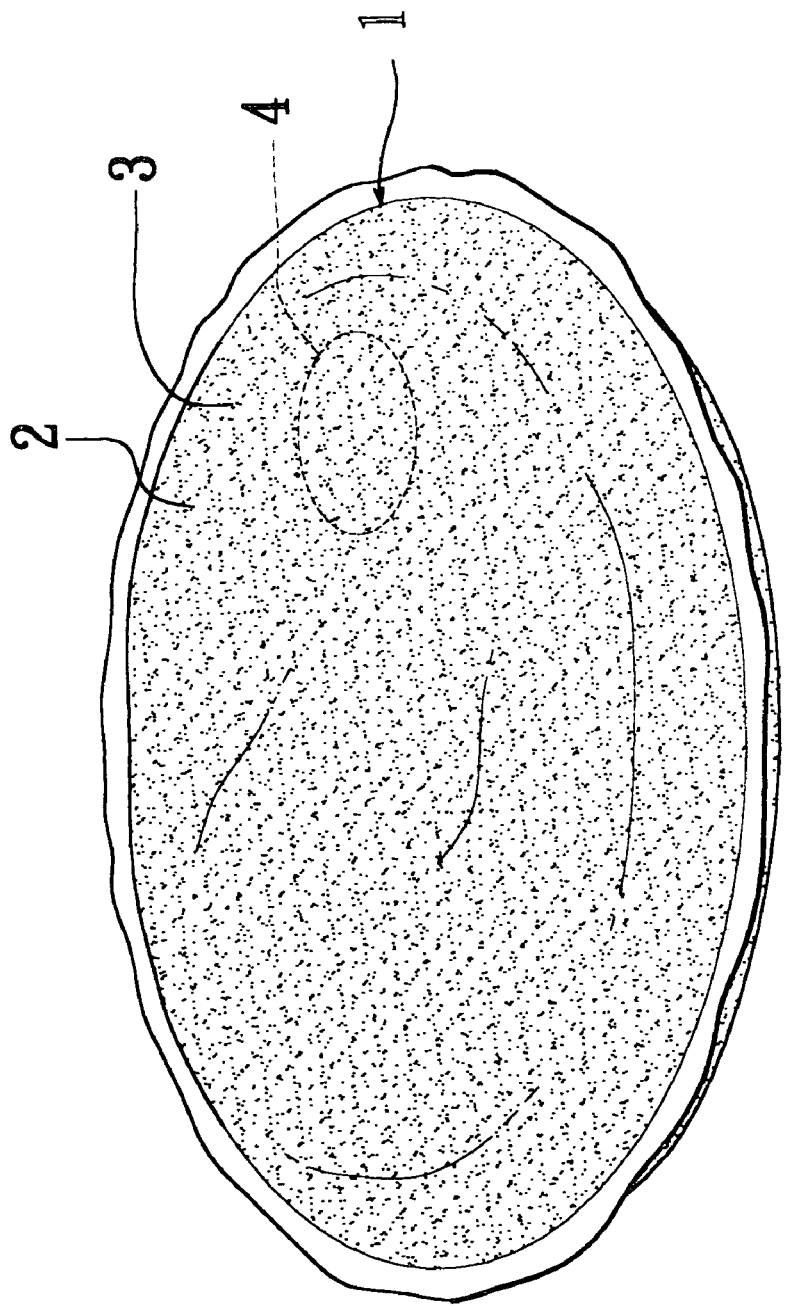
FIG. 1 is a perspective view of the thermo chromic heat storing/releasing device according to a preferred embodiment of the present invention.
Figure 2:
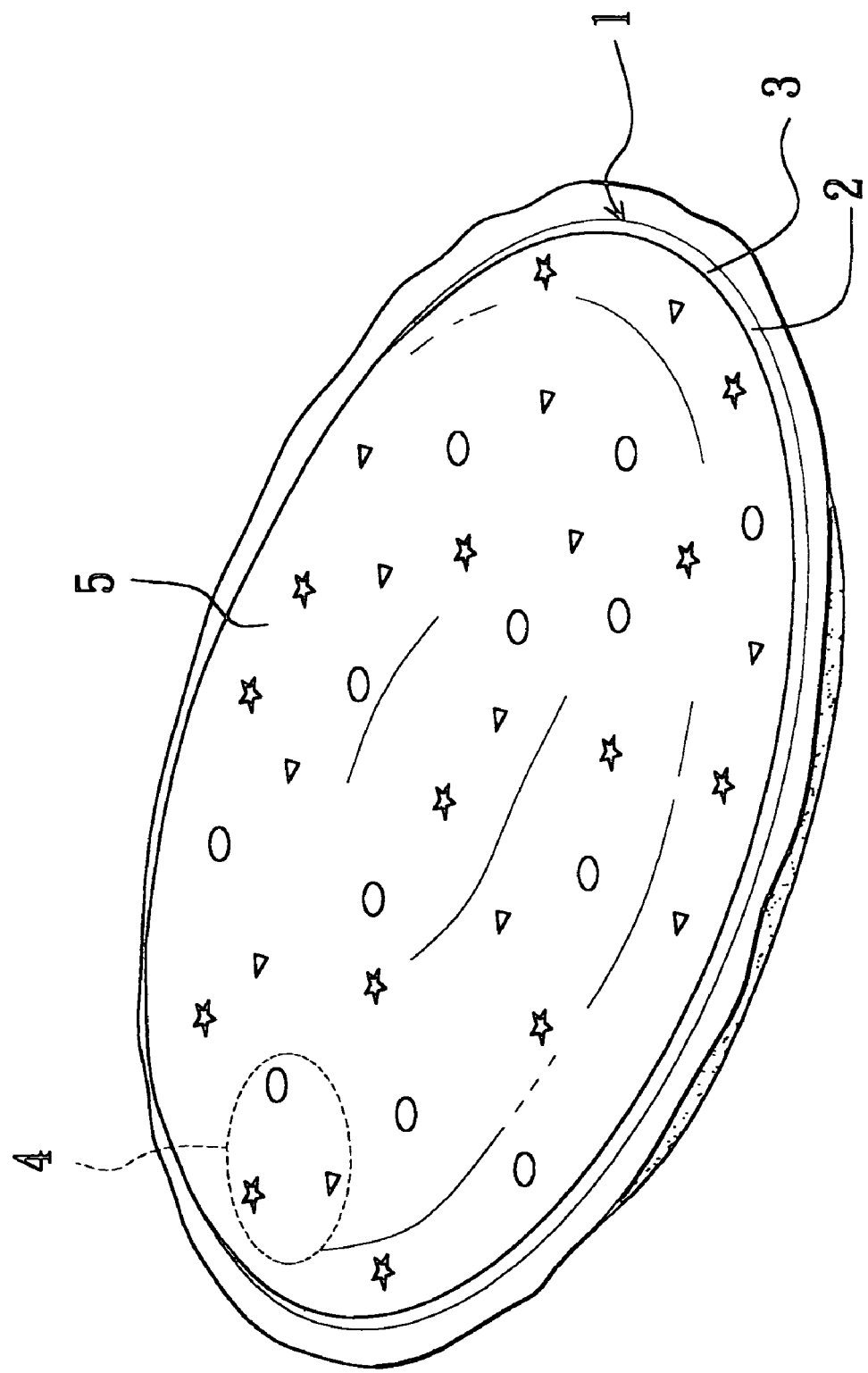
FIG. 2 is a perspective view of the thermo chromic heat storing/releasing device according to another preferred embodiment of the present invention.

To further disclose the technical characteristics of the invention, please refer to the FIGS. The primary objective of the present invention is to provide a thermo chromic heat storing/releasing device that comprises a bag 1, a heat storing/releasing material 2 contained in the bag 1, a thermo chromic material 3, and/or a starter 4.

In the present invention, a bag 1 is made of a polymer material and preferably transparent but not limited to such. Basically, the bag 1 can be used repeatedly, and thus it is better to select a durable and flexible material with a certain specific thickness, so that the edges of the finished goods of the bag 1 can be sealed by high frequency or other equivalent measures. However, the sealing is a prior art and will not be described here.

Unlike the prior art, the present invention achieves the thermo chromic effect by mixing a thermo chromic material 3 in the foregoing heat storing/releasing device, and the thermo chromic material 3 is a chemical dye which will fade when heated. In other words, the color of the thermo chromic material 3 changes as the temperature rises or drops, and the temperature for changing the color is predetermined. For example, the color of the thermo chromic material 3 changes color at a high temperature and resumes its original color at a low temperature. The thermo chromo material 3 of this sort is made by local and foreign manufacturers, wherein the "Thermochromic Capsule Powder" produced by local manufactures is composed of a "fluoran leuco dye plus polymer melanine/formaldehyde for capsule", and thus it could be in various different colors and the range of its temperature is set from −15° C. to 70° C. according to the user's requirements. The preferred embodiment of the invention adopts but not limited to such thermo chromic material 3.

The thermo chromic material 3 could be single colored, double colored or multi-colored. For the single colored thermo chromic material 3, if the thermo chromic material 3 is blue in color, then the color of the heat storing/releasing device is blue at regular room temperature. However, after it is heated, the thermo chromic material 3 is changed to colorless. Therefore, when the heat is released, the heat storing/releasing device shows a light color such as a light blue color or even colorless. However, when the temperature drops to a predetermined normal temperature, the heat storing/releasing device resumes the blue color. Such setting also can apply to other colors including black.

As to the event of two mixed colors such as yellow and blue, the two colors are combined to produce a green color according to the chromatology. If yellow is set as the faded color, the yellow color will fade and turn into a blue color when releasing the heat (or the temperature rises). After the heat is released, the yellow color is resumed and the overall color is turned into green to constitute a "blue outside and green inside" phenomenon.

Therefore, one or more color can be used for the event of mixed colors according to the temperature.

The proportion of the mixed colors depends on the requirements of the change of color. Basically, the more the thermo chromic material, the larger is the change. For the case of a single color, the proportion should be not less than 5% of the total weight; for the case of a multiple of colors, the total weight of the thermo chromic material 3 should not be less than 5% after the colors are mixed.

If a saturated sodium acetate solution is used, the heat is not released, or the temperature is not dropped naturally as the water solution does as described previously, then a starter 4 can be added. The starter 4 is a metal plate, which can be bent by an external force to produce a microwave to activate the heat storing/releasing material 2 to increase its temperature and release heat, and then drops its temperature. Since it is a prior art, and thus will not described here.

The technical measure of mixing the thermo chromic material 3 into a heat storing/releasing material 2 according to the present invention allows users to know about the current temperature of the heat storing/releasing device visually by the change of color. The present invention can be considered as a big breakthrough on the application of a heat storing/releasing device by providing a quick way of knowing about its temperature visually.

Besides mixing the thermo chromic material 3 into a heat storing/releasing material 2, the change of the thermo chromic material 3 can be applied simply on the printed layer 5 of the bag 1 of the heat storing/releasing device 2. In other words, if the printing material is mixed with the thermo chromic material 3 and printed onto the inner surface or the outer surface of the bag 1, then it can achieve the effect of changing colors in correspondence with the change of temperature, and includes the change of a single color, two colors or several colors. The printing is printed on the whole surface with decorative text and/or graphic patterns. However, the printing skill is a prior art, and thus will not be described here.

Further, please refer to FIG. 3 for the heat storing/releasing device of the present invention. A cover 6 made of a material including polymer, woven cloth, unwoven cloth or knitted bag is added to accommodate the heat storing/releasing device and constitute a covered printed layer 61 comprised of a thermo chromic material mixed with a printed material. Therefore, even if the heat storing/releasing device is placed into the cover 6, the covered printed layer 61 can still achieve the visual thermo chromic effect.

Therefore, the heat storing/releasing device can achieve the effect of sensing the change of temperature according to the foregoing two embodiments and be set into a single section or two or more sections for the change of temperature. Besides providing the thermo chromic effect by the change of color, the heat storing/releasing device also has several colors for the visual effect, and thus providing diversified choices for users. If other fillers or additives such as fluorescent powders are mixed, the cost can be lowered.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements.

What is claimed is:

1. A heat storing/releasing device, comprising: a bag, having an enclosed space accommodating a heat storing/releasing material and a thermo chromic material capable of storing and releasing heat; and at least one visible color of said thermo chromic material changing according to temperature and said thermo chromic material being mixed with said heat storing/releasing material and disposed in said bag; thereby said thermo chromic material changes its color for a visual inspection as temperature changes,
   wherein said heat storing/releasing material is a saturated sodium acetate solution and said bag further comprises a starter.

2. The heat storing/releasing device of claim 1, wherein said bag is made of a polymer material.

3. A heat storing/releasing device, comprising: a bag, having an enclosed space accommodating a heat storing/releasing material and a thermo chromic material capable of storing and releasing heat; and a thermo chromic printed layer, being at least partially disposed in said bag, and having a dye made of a thermo chromic material mixed in a printed material; thereby said thermo chromic material changes its visible color for a visual inspection as temperature changes,
   wherein said heat storing/releasing material is a saturated sodium acetate solution and said bag further comprises a starter.

4. The heat storing/releasing device of claim 3, wherein said bag is made of a polymer material.

5. The heat storing/releasing device of claim 3, wherein said printed layer is disposed on a whole surface of said bag.

6. A heat storing/releasing device, comprising: a bag, having an enclosed space accommodating a heat storing/releasing material and a thermo chromic material capable of storing and releasing heat; and a cover, having a space for accommodating said bag and covering at least a part of a printed layer, and said printed material of said covered printed layer being mixed with a dye made of a thermo chromic material; thereby said covered printed layer changes its visible color as temperature changes,
   wherein said heat storing/releasing material is a saturated sodium acetate solution and said bag further comprises a starter.

7. The heat storing/releasing device of claim 6, wherein said cover is made of a material selected from the group consisting of a polymer material, a woven cloth, an unwoven cloth, and a fabric.

* * * * *